United States Patent [19]

Kathawala

[11] 3,946,119

[45] Mar. 23, 1976

[54] OPTIONALLY SUBSTITUTED α-TERTIARY BUTYL-P-PHENOXYBENZYLAMINES AND THEIR USE AS HYPOLIPIDEMIC AGENTS

[75] Inventor: Faizulla G. Kathawala, West Orange, N.J.

[73] Assignee: Sandoz, Inc., E. Hanover, N.J.

[22] Filed: Dec. 23, 1974

[21] Appl. No.: 535,436

[52] U.S. Cl....... 424/330; 260/570.8 R; 260/590 D; 424/360; 424/361; 424/363; 424/365
[51] Int. Cl.² ........................................ H61K 31/135
[58] Field of Search............... 260/570.8 R; 424/330

[56] References Cited
UNITED STATES PATENTS

| | | | |
|---|---|---|---|
| 3,225,098 | 12/1965 | Krohs et al. | 260/570.8 R |
| 3,245,878 | 4/1966 | Berger et al. | 424/330 |
| 3,547,999 | 12/1970 | Shulgin | 260/570.8 R |
| 3,772,370 | 11/1973 | Surrey | 424/330 X |

Primary Examiner—Jerome D. Goldberg
Assistant Examiner—Vera C. Clarke
Attorney, Agent, or Firm—Gerald D. Sharkin; Richard E. Vila; Joseph J. Borovian

[57] ABSTRACT

Hypolipidemic agents of the formula:

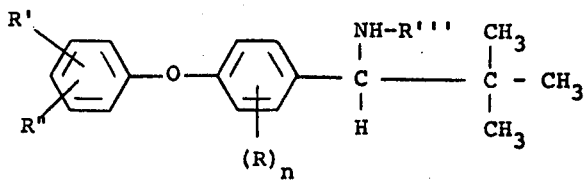

wherein
R is hydrogen, alkyl or halo,
R' and R'' are hydrogen, halo, alkyl or alkoxy,
R''' is alkyl, and
$n$ is 1 or 2.

19 Claims, No Drawings

OPTIONALLY SUBSTITUTED α-TERTIARY BUTYL-P-PHENOXYBENZYLAMINES AND THEIR USE AS HYPOLIPIDEMIC AGENTS

The present invention relates to optionally substituted α-tertiary butyl-p-phenoxybenzylamines, acid addition salts thereof and to their use as hypolipidemics. The invention also relates to pharmaceutical compositions containing the above compounds as an active ingredient thereof and to the method of using such compositions for the treatment of lipidemia.

The compounds with which this invention is concerned may be represented by the following structural formula:

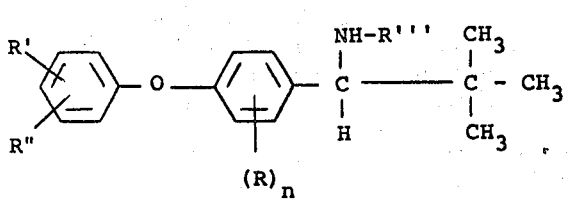

wherein
R is hydrogen, alkyl of 1 to 4 carbon atoms, or halo of atomic weight of from 18 to 36,
R' and R'' are independently hydrogen, halo of atomic weight of from 18 to 36, alkyl of 1 to 4 carbon atoms or alkoxy of 1 to 4 carbon atoms,
R''' is alkyl of 1 to 5 carbon atoms, and
$n$ is 1 or 2.

The compounds of formula (I) may be prepared by the following reaction scheme:

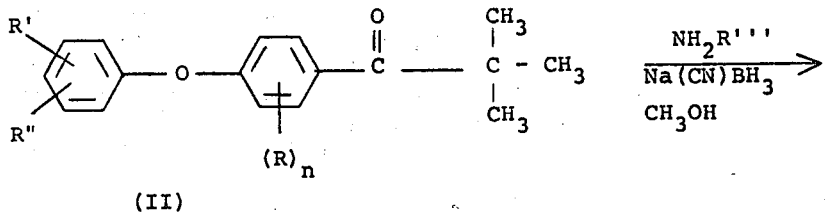

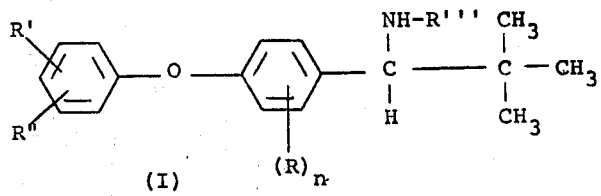

wherein R, R', R'', R''' and $n$ are as defined above. This process is conducted by reacting (II) with NH$_2$R''' and sodium cyanoborohydride in the presence of a lower alkanol at temperatures in the range of 10°C. to 35°C., preferably at room temperature, for a period of time between 48 and 72 hours. Suitable lower alkanols are methanol, ethanol, isopropanol and the like, preferably methanol.

The compounds (I) are also preparable by the following reaction scheme:

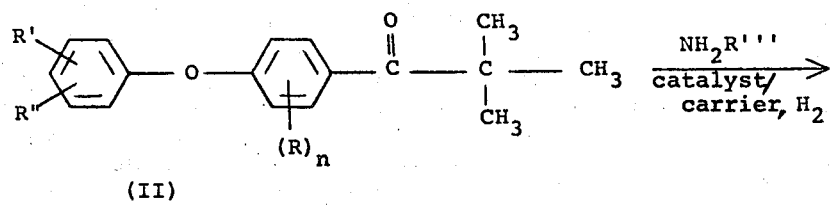

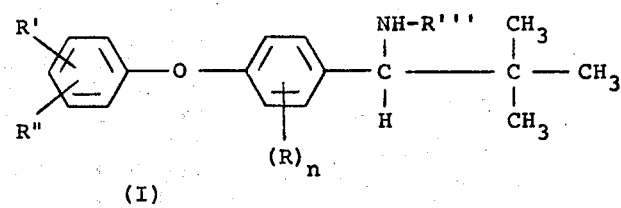

wherein R, R', R'', R''' and $n$ are as defined above. This process is conducted by reacting (II) with NH$_2$R''' while hydrogenating the reaction system in the presence of a hydrogenation catalyst and an inert, organic solvent at a temperature within the range of 10°C. to 50°C., preferably 35°C. to 50°C., for a period of time between 12 and 60 hours. The reaction is conveniently commenced at about room temperature in a hydrogen atmosphere at normal pressure for 12 to 24 hours, and the reaction mixture then heated to a temperature in the range of 35°C. to 50°C., for a period of time between 12 and 48 hours at a hydrogen pressure of between 2 and 5 atmospheres, to effect complete reaction. As suitable hydrogenation catalysts, metal hydrogenation catalysts, preferably employed in finely dispersed form, offering as large an active surface as possible, may be employed, particularly noble metal catalysts, e.g., palladium, platinum, ruthenium and rhodium, which may be employed with a carrier such as barium sulphate, strontium carbonate, calcium carbonate, silicon dioxide, aluminum sesquioxide and particularly active charcoal. Suitable inert, organic solvents include lower alkanols, e.g., methanol, ethanol, isopropanol and the like, dimethyl formamide or dimethyl acetamide, preferably ethanol.

The compounds of formula (II) may be prepared by reacting a compound of the formula (III):

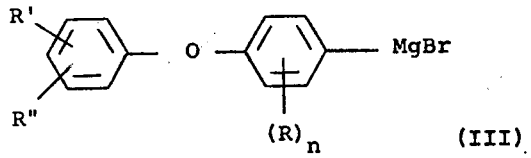

in which R, R', R'' and $n$ are as defined, with a compound of the formula (IV):

and hydrolyzing the resulting product. The reaction may be carried out at temperatures in the range of from 0°C. to 100°C. The reaction is conveniently carried out in the presence of an inert, organic solvent of conventional type including the cyclic and acyclic ethers, such as diethyl ether and tetrahydrofuran.

The hydrolysis may be effected under alkaline, neutral or acid conditions, preferably mild acidic conditions, suitably using hydrochloric or sulfuric acid, preferably hydrochloric acid. The hydrolysis may be carried out conveniently at a temperature of from −40° to 100°C., preferably at a temperature of from 10°C to 30°C.

The compounds of formula (III) may be prepared by reacting a compound of the formula (V):

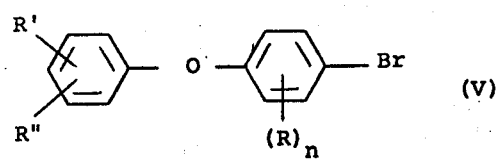

in which R, R', R'' and $n$ are as defined, with magnesium in a conventional manner for preparation of a Grignard compound from the corresponding bromo compound.

Certain of the compounds of the formula (V) are known and may be prepared by methods disclosed in the literature. Those compounds not specifically disclosed may be prepared by analogous methods from known starting materials.

The compounds of formula (I) may be recovered using conventional techniques such as crystallization, filtration or column chromatography.

Compounds of formula (I) also form non-toxic pharmaceutically acceptable acid addition salts. Such salts are prepared by reacting the base with an appropriate acid and, accordingly, are included within the scope of the invention. Representative of such salts are the mineral acid salts, such as the hydrochloride, hydrobromide, sulfate, phosphate and the like, and the organic acid salts, such as the succinate, benzoate, acetate, p-toluenesulfonate, benzenesulfonate, maleate, malate, tartrate, methanesulfonate, cyclohexylsulfamate and the like.

As previously indicated, the compounds of formula (I) and their acid addition salts are useful because they possess pharmacological activity in animals, e.g., mammals. In particular, the compounds of formula (I) are useful as hypolipidemic agents in the treatment of lipidemia, in particular, hyperlipoproteinemia as indicated by the fall in cholesterol and/or triglyceride levels in male albino Wistar rats weighing 110–130 g. initially. The rats are maintained on drug-free laboratory chow diet for seven days and then divided into groups of 8 to 10 animals. Each group with the exception of the control is then given the compound orally at a dose of 7.5, 30, 250 or 500 milligrams per kilogram of body weight per day, p.o. for six days. At the end of this period, the animals are anesthetized with sodium hexobarbital and bled from the carotid arteries. Serum or plasma samples are then extracted with isopropanol, and the cholesterol content of the extracts is estimated on a Technicon Autoanalyzer by standard methodology. For example, 1.0 ml. of serum is added to 9.0 ml. redistilled isopropanol. Two autoanalyzer cupsful of a mixture of zeolite-copper hydroxide and Lloydds reagent (Kessler, G., and Lederer, H., 1965, Technicon Symposium, Mediad Inc., New York, 345–347) are added; and the mixture is shaken for 1 hour. Cholesterol levels are determined using this sample by the standard Technicon N 24A (cholesterol) methodology. The mean total serum cholesterol levels are then computed and the hypocholesterolemic activity is expressed as the fall in cholesterol levels as a percentage of the control level. For the triglyceride determination, blood samples are collected as above and 1.0 ml. samples of the serum are added to 9.0 ml. redistilled isopropanol. Two autoanalyzer cupsful of a mixture of zeolite-copper hydroxide and Lloydds reagent (Kessler, G., and Lederer, H., 1965 Technicon Symposium, Mediad Inc., New York, 345–347) are added; and the mixture is shaken for 1 hour. After centrifugation, 2 ml. of the clear supernates are evaporated to dryness and saponified by addition of 0.1 ml. 10% KOH in 90% ethanol and 1.0 ml. Skelly B (petroleum ether b.p. 60°–70°C.). After acidification and the removal of fatty acids with petroleum ether, the aqueous phases are neutralized, suitably diluted with water, and analyzed for glycerol by the method of Lofland (Anal. Biochem. 9, 393, 1964) using the Technicon Autoanalyzer. The change in serum triglyceride levels induced by the drug is computed as a percentage of the control triglyceride levels.

For such usage, the compounds may be administered orally or parenterally, preferably orally, and in admixture with conventional pharmaceutical carriers. The anti-hyperlipidemic effective dosage of the compounds of formula (I) employed for the alleviation of lipidemia may vary depending on the particular compound employed and the severity of the condition being treated. In general, satisfactory results are obtained when administered at a daily dosage of from about 4 milligrams to about 250 milligrams per kilogram of animal body weight, preferably given orally and in divided doses, 2 to 4 times a day, or in sustained release form. For most mammals, the total daily dosage is from about 300 milligrams to about 3000 milligrams of the compound, and dosage forms suitable for internal administration comprise from about 75 to 1500 milligrams of the compound in admixture with a solid or liquid pharmaceutically acceptable carrier or diluent.

For above usage, the compounds of formula (I) may be administered orally in such forms as tablets, dispersible powders, granules, capsules, syrups and elixirs; and parenterally as solutions, suspensions, dispersions, emulsions, and the like, e.g., a sterile injectable solution such as an aqueous suspension. These pharmaceutical preparations may contain 0.5% up to about 90% of the active ingredient in combination with the carrier or adjuvant, more usually between 3% and 50% by weight. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium phosphate, calcium sulphate dihydrate, lactose and talc, granulating and disintegrating agents, e.g., starch and alginic acid, binding agents, e.g., starch, gelatin, polyvinyl pyrrolidone and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert liquid or solid diluent, e.g., calcium carbonate, calcium phosphate, kaolin, peanut oil, sesame oil and corn oil. The preferred pharmaceutical compositions from the standpoint of preparation and ease of administration are solid compositions, particularly hard-filled capsules and tablets.

Capsules containing the ingredients indicated below may be prepared by conventional techniques and are useful in treating lipidemia, particularly hyperlipoproteinemia, in mammals at a dose of one capsule, 2 to 4 times a day.

| Ingredients | Weight (mg.) |
| --- | --- |
| α-tertiary butyl-N-methyl-p-phenoxybenzylamine | 150 |
| peanut or sesame oil | 200 |

-continued

| Ingredients | Weight (mg.) |
| --- | --- |
| Total | 350 mg. |

The following examples are merely illustrative of specific compounds of the invention and the manner in which they may be prepared.

EXAMPLE 1

α-Tertiary butyl-N-methyl-p-phenoxybenzylamine

A mixture of 10 g. of 4-phenoxy-pivalophenone, 1.5 g. of sodium cyanoborohydride and 7.4 g. of methylamine in 60 ml. of methanol and 2 ml. of methanolic 4N hydrochloric acid is stirred at room temperature for 72 hours. The reaction mixture is then filtered to remove any insoluble material and the filtrate is evaporated in vacuo, after which the resultant residue is treated with 2N hydrochloric acid solution and ether. The resultant water insoluble hydrochloride of the desired product is then filtered off and washed well with ether. The hydrochloride is then suspended in 2N sodium hydroxide solution and extracted several times with ethyl acetate. The combined ethyl acetate extracts are dried over sodium sulfate, filtered, and evaporated in vacuo to give the desired crude oil. This oil, being a high boiling liquid, is purified by distillation under high vacuum to obtain α-tertiary butyl-N-methyl-p-phenoxybenzylamine, b.p. 166°–176°C. at 0.1 mm/Hg. (m.p. of hydrochloride, 278°–279°C.).

EXAMPLE 2

Following essentially the procedure of Example 1, and using in place of methylamine, an equivalent amount of:
 a. ethylamine,
 b. isopropylamine, and
 c. propylamine,
there is obtained
 a. α-tertiary butyl-N-ethyl-p-phenoxybenzylamine,
 b. α-tertiary butyl-N-isopropyl-p-phenoxybenzylamine, and
 c. α-tertiary butyl-N-propyl-p-phenoxybenzylamine, respectively.

EXAMPLE 3

Following essentially the procedure of Example 1, and using place of 4-phenoxy-pivalophenone, an equivalent amount of:
 a. 4-(p-methoxyphenoxy)-pivalophenone,
 b. 4-(m-chlorophenoxy)-pivalophenone,
 c. 4-(p-methylphenoxy)-pivalophenone,
 d. 4-phenoxy-3-methyl-pivalophenone,
 e. 4-phenoxy-3,5-dichloro-pivalophenone, and
 f. 4-(p-methoxyphenoxy)-3-chloro-pivalophenone,
there is obtained
 a. α-t-butyl-N-methyl-4-(p-methoxyphenoxy)benzylamine,
 b. α-t-butyl-N-methyl-4-(m-chlorophenoxy)benzylamine,
 c. α-t-butyl-N-methyl-4-(p-methylphenoxy)benzylamine,
 d. α-t-butyl-N-methyl-4-phenoxy-3-methylbenzylamine,
 e. α-t-butyl-N-methyl-4-phenoxy-3,5-dichlorobenzylamine, and f. α-t-butyl-N-methyl-4-(p-methoxyphenoxy)-3-chlorobenzylamine, respectively.

EXAMPLE 4

α-Tertiary butyl-N-methyl-p-phenoxybenzylamine

To a solution of 25 g. of 4-phenoxy-pivalophenone, and 15 g. of methylamine in 500 ml. of ethanol is added 5.0 g. of hydrogenation catalyst (10% Pd on active charcoal). The resultant mixture is then hydrogenated under a hydrogen blanket at room temperature and atmospheric pressure for about a 12-hour period. The reaction mixture is then heated to 45°C. and hydrogenation continued for an additional 48 hours, or until the theoretical uptake of hydrogen is achieved. The reaction mixture is then filtered to remove the palladium and the solvent is removed in vacuo. The resultant residue is then boiled in 250 ml. of 2N hydrochloric acid for 2 hours (to hydrolyze any undesired imine) and the water insoluble hydrochloride of the desired product is filtered and washed well with ether. The hydrochloride is then suspended in 2N sodium hydroxide solution and extracted several times with ethyl acetate. The combined ethyl acetate extracts are dried over sodium sulfate, filtered and evaporated in vacuo to give the desired crude oil. This oil, being a high boiling liquid, is purified by distillation under high vacuum to obtain α-tertiary butyl-N-methyl-p-phenoxybenzylamine, b.p. 166°–176°C. at 0.1 mm/Hg.

EXAMPLE 5

Preparation of 4-phenoxy-pivalophenone

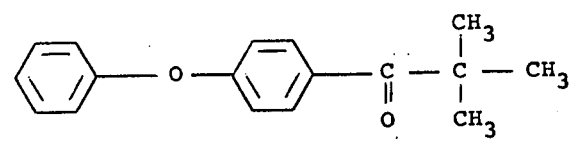

To a flask containing 33.6 g. of magnesium and crystals of iodine, is added 50–70 ml. of a solution of 300 g. of (p-bromophenyl)phenyl ether in 500 ml. of tetrahydrofuran. The remainder of the solution is added as need to maintain a gentle reflux and the resulting mixture heated to reflux for 30 minutes. The resulting mixture is then added to a solution of trimethylacetyl chloride in 500 ml. of tetrahydrofuran at a rate to maintain 40°–50°C. The resulting mixture is then stirred at ambient temperature for one hour and then 200 ml. of 2N hydrochloric acid is added. The organic layer is washed twice with one liter of 2N sodium carbonate solution, dried and evaporated in vacuo to a liquid weighing about 290 g. This liquid is distilled under reduced pressure to obtain 4-phenoxypivalophenone, b.p. 136°–139°C. at 0.1 mm/Hg.

What is claimed is:

1. A compound of the formula:

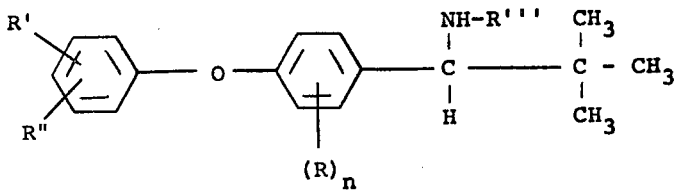

wherein
R is hydrogen, alkyl of 1 to 4 carbon atoms, or halo of atomic weight of from 18 to 36,
R' and R'' are independently hydrogen, halo of atomic weight of from 18 to 36, alkyl of 1 to 4 carbon atoms, or alkoxy of 1 to 4 carbon atoms,
R''' is alkyl of 1 to 5 carbon atoms, and
n is 1 or 2,
or a pharmaceutically acceptable acid addition salt thereof.

2. A compound of claim 1 having the formula:

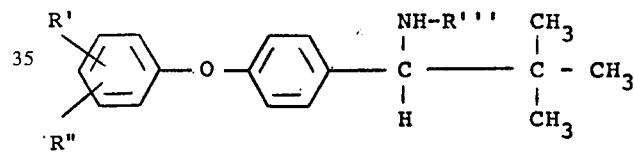

wherein R', R'' and R''' are as defined in claim 1, or a pharmaceutically acceptable acid addition salt thereof.

3. A compound of claim 2 having the formula:

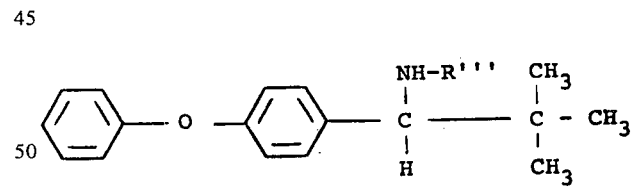

wherein R''' is as defined in claim 2, or a pharmaceutically acceptable acid addition salt thereof.

4. The compound of claim 3 which is α-tertiary butyl-N-methyl-p-phenoxybenzylamine.

5. The compound of claim 3 which is α-tertiary butyl-N-isopropyl-p-phenoxybenzylamine.

6. The compound of claim 3 which is α-tertiary butyl-N-propyl-p-phenoxybenzylamine.

7. A pharmaceutical composition in unit dosage form for treating lipidemia in mammals comprising an inert pharmaceutically acceptable carrier and from 75 to 1500 milligrams of a compound of the formula:

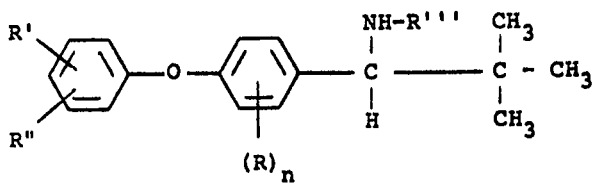

wherein
R is hydrogen, alkyl of 1 to 4 carbon atoms, or halo of atomic weight of from 18 to 36,
R' and R" are independently hydrogen, halo of atomic weight of from 18 to 36, alkyl of 1 to 4 carbon atoms, or alkoxy of 1 to 4 carbon atoms,
R''' is alkyl of 1 to 5 carbon atoms, and
n is 1 or 2,
or a pharmaceutically accpetable acid addition salt thereof.

8. A composition in accordance with claim 7 in which the compound is of the formula:

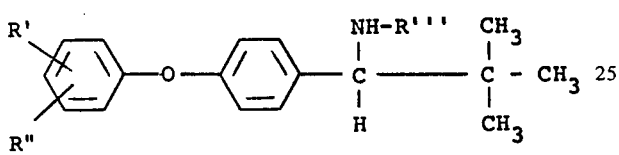

wherein R', R" and R''' are as defined in claim 7, or a pharmaceutically acceptable acid addition salt thereof.

9. A composition in accordance with claim 8 in which the compound is of the formula:

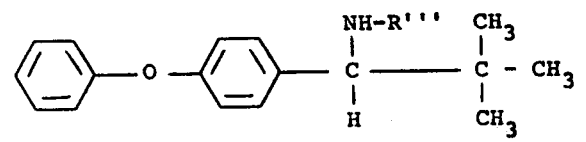

wherein R''' is as defined in claim 8, or a pharmaceutically acceptable acid addition salt thereof.

10. A composition in accordance with claim 9 in which the compound is α-tertiary butyl-N-methyl-p-phenoxybenzylamine.

11. A composition in accordance with claim 9 in which the compound is α-tertiary butyl-N-isopropyl-p-phenoxybenzylamine.

12. A composition in accordance with claim 9 in which the compound is α-tertiary butyl-N-propyl-p-phenoxybenzylamine.

13. The method for treating a mammal having lipidemia comprising administering a hypolipidemic effective amount to said mammal of a compound of the formula:

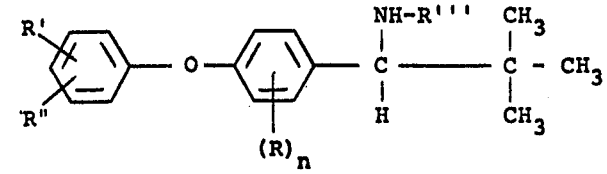

wherein
R is hydrogen, alkyl of 1 to 4 carbon atoms, or halo of atomic weight of from 18 to 36,
R' and R" are independently hydrogen, halo of atomic weight of from 18 to 36, alkyl of 1 to 4 carbon atoms, or alkoxy of 1 to 4 carbon atoms,
R''' is alkyl of 1 to 5 carbon atoms, and
n is 1 or 2,
or a pharmaceutically acceptable acid addition salt thereof.

14. A method in accordance with claim 13 in which the compound is administered in a daily amount of from 300 to 3000 milligrams.

15. A method in accordance with claim 13 in which the compound administered is a compound of the formula:

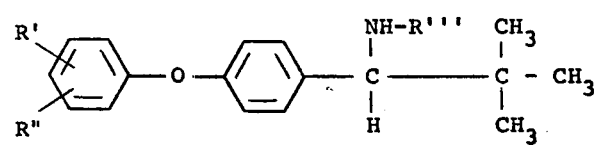

wherein R', R" and R''' are as defined in claim 13, or a pharmaceutically acceptable acid addition salt thereof.

16. A method in accordance with claim 15 in which the compound administered is a compound of the formula:

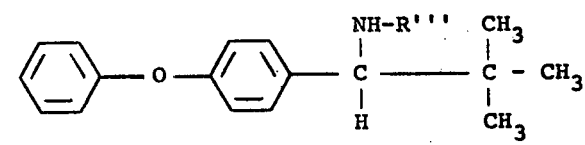

wherein R''' is as defined in claim 15, or a pharmaceutically acceptable acid addition salt thereof.

17. A method in accordance with claim 16 in which the compound administered is α-tertiary butyl-N-methyl-p-phenoxybenzylamine.

18. A method in accordance with claim 16 in which the compound administered is α-tertiary butyl-N-propyl-p-phenoxybenzylamine.

19. A method in accordance with claim 16 in which the compound administered is α-tertiary butyl-N-cyclopropyl-p-phenoxybenzylamine.

* * * * *